United States Patent [19]
Knight et al.

[11] Patent Number: 6,046,241
[45] Date of Patent: Apr. 4, 2000

[54] β-ALETHINE AS ANTI-TUMOR AGENT

[75] Inventors: Galen D. Knight; Paul L. Mann; Terrance J. Scallen, all of Albuquerque, N.Mex.

[73] Assignee: University of New Mexico, Albuquerque, N.Mex.

[21] Appl. No.: 08/468,043

[22] Filed: Jun. 6, 1995

Related U.S. Application Data

[60] Continuation of application No. 08/316,836, Oct. 3, 1994, Pat. No. 5,643,966, which is a division of application No. 07/924,977, Aug. 5, 1992, abandoned, which is a continuation-in-part of application No. 07/549,103, Jul. 6, 1990, abandoned.

[51] Int. Cl.$^7$ .......................... A61K 31/16; A61K 39/00; C12N 15/00
[52] U.S. Cl. .................... 514/626; 424/277.1; 435/172.1
[58] Field of Search ...................... 435/172.1; 424/277.1; 514/626

[56] References Cited

U.S. PATENT DOCUMENTS

| | | |
|---|---|---|
| 2,835,704 | 5/1958 | Walton . |
| 4,552,765 | 11/1985 | Mita et al. . |
| 5,013,546 | 5/1991 | Gottlieb et al. . |

FOREIGN PATENT DOCUMENTS

| | | |
|---|---|---|
| WO 85/00167 | 1/1985 | WIPO . |
| WO 92/00960 | 1/1992 | WIPO . |

OTHER PUBLICATIONS

Oiry et al, "Synthesis and Radioprotective Activity of New Cysteamine and Cystamine Derivatives", J. Med. Chem. 29(11):2217–2225 (1986).

Komoriya et al, "Anti–Arthritic and Immunoregulatory Effects of TI–31 on Collagen–Induced Arthritis", Japan. J. Pharmacol. 45:389–396 (1987).

Komoriya et al, "Inhibitory effect of TI–31 on autoimmune nephritis in B/NZW $F_1$ mice through regulation of the immune response", Immunopharmacology 13:89–98 (1987).

Waldmann, "Monoclonal Antibodies in Diagnosis and Therapy", Science 252:1657–1662 (1991).

Roederer et al, "Cytokine–stimulated human immunodificiency virus replication is inhibited by N–acetyl–L–cystine", Proc. Natl. Acad. Sci. USA 87:4884–4888 (1990).

Foon, "Biological Response Modifiers: The New Immunotherapy", Cancer Research 49:1621–1639 (1989).

Osband et al, "Problems in the investigational study and clinical use of cancer immunotherapy", Immunology Today 11(6):193–195 (1990).

Immunology Second Edition, edited by Jean–Francois Bach, M.D., D.Sc., pp. 88–105. (1990).

Stalb et al, "Protection against Experimental Cerebral Metastases of Murine Melanoma B16 by Active Immunization", Cancer Research 53:1113–1121 (1993).

Current Protocols in Immunology, edited by John E. Coligan (1991).

Sachs, "Growth, Differentiation and the Reversal of Malignancy", Scientific American, pp. 40–47 (1986).

Cockroft, "Nutrient requirements of rat embryos undergoing organogenesis in vitro", J. Reprod. Fert. 57:505–510 (1979).

Droge et al, "Modulation of Lymphocyte Functions and Immune Responses by Cysteine and Cysteine Derivatives", The American Journal of Medicine 91(suppl 3C):3C–140S (1991).

*Primary Examiner*—Jerome D. Goldberg
*Attorney, Agent, or Firm*—Judith A. Evans, Esq.; Dovetail Technologies, Inc.

[57] ABSTRACT

β-alethine is identified as an anti-tumor agent.

19 Claims, 9 Drawing Sheets

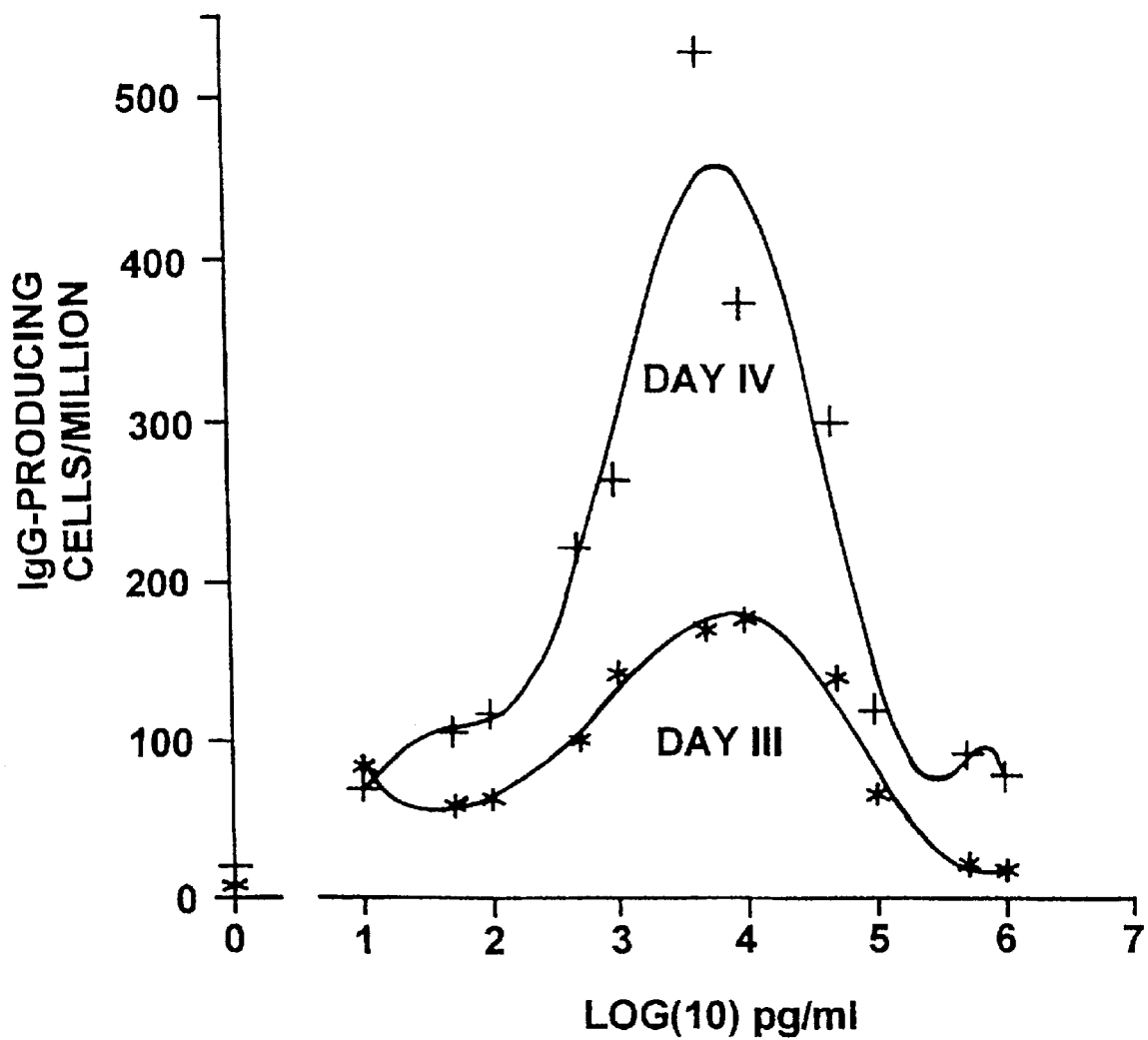

β-ALETHINE AS ANTI-TUMOR AGENT

This is a continuation of application Ser. No. 08/316,836, filed Oct. 3, 1994, now U.S. Pat. No. 5,643,966 which is a divisional of Ser. No. 07/924,977, filed Aug. 5, 1992, now abandoned which is a CIP of Ser. No. 07/549,103, filed Jul. 6, 1990 now abandoned.

GOVERNMENT RIGHTS

This invention was made in the performance of work under grants #HL 16,796, #AM 10,628, and #SO7RR-05583-25 with the National Institutes of Health, and the United States Government has certain rights therein.

1. BACKGROUND OF THE INVENTION

The invention provides a method for treating neoplasias with β-alethine. In particular, the invention provides methods for treating a variety of neoplasias which reduce tumor burden, inhibit tumor growth, and inhibit tumor intravascularization, for example from metastasizing tumors. β-alethine has been identified as a compound inducing cell differentiation and modulating cell growth, phenotypic expression (including bioproduction and function), vitality, and longevity in copending application SN entitled "Beta-Alethine Use in Cell Culture and Therapy"; a correspondence between cell differentiation and reversal of malignancy has been suggested; see, for example, "Growth, Differentiation, and the Reversal of Malignancy", *Scientific American* pp. 40–47, January, 1986, and the publications cited therein.

The present application relates to the identification of β-alethine as a non-cell-lineage-dependent anti-tumor compound, and the use of β-alethine to induce normalization of the function of a variety of neoplastic cells, particularly for therapeutic benefits.

2. DISCUSSION OF RELATED ART

β-alethine is known to be produced in vivo as a by-product of metabolic pathways. It is related via these pathways to pantothenic acid, which is a vitamin having known nutritional benefits (see, e.g., *J.Reprod.Fert.* 57: 505–510 (1979), and related compounds have been suggested for use in conjunction with radiotherapy as radioprotectors (*J.Med.Chem.* 29: 2217–2225, 1986; WO 35/00157, Jan. 17, 1985). No other relevant asserted biological functions of this compound are known to be described in the prior art. The compound is primarily well-known as a starting material for the chemical synthesis of related compounds (see, e.g., Japanese patent applications (83) 198461; (83) 46063A2; (81) 156256A2; (81) 104861A2; (80) 124755; (75) 62932; (80) 07222; and U.S. Pat. Nos. 2,835,704 and 4,552,765; for examples of the preparation of β-alethine, β-aletheine, and pantetheine, and derivatives and intermediates of these compounds, used in the synthesis of coenzyme A and its analogues).

3. SUMMARY

The invention accordingly provides methods for the recognition, normalization, and elimination of neoplastic cells particularly for the treatment of cancer. Within the scope of the present invention, β-aletheine, the reduced form of β-alethine, is to be considered the biological equivalent of β-alethine for purposes of practicing the invention, as β-alethine is readily reduced to β-aletheine in vivo, for example by abundant intracellular thiol compounds, such as glutathione in mammals, including humans. Both compounds have the advantage of having inherent antioxidative properties; however, β-alethine is chemically more resistant to autoxidation than β-aletheine, and the use of β-alethine in the present invention is generally preferred for this reason.

4. BRIEF DESCRIPTION OF THE DRAWING

Figure 7:
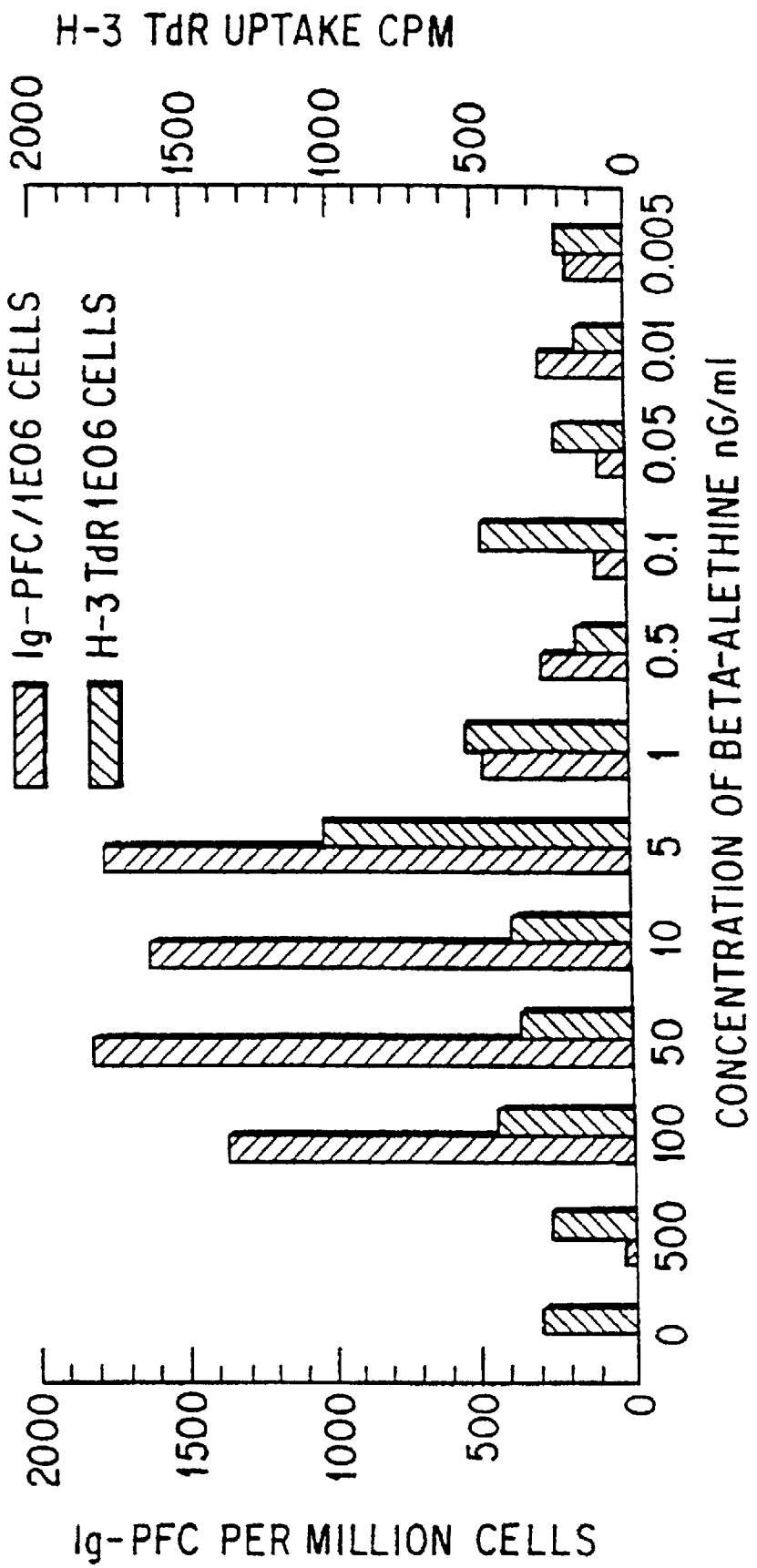
Figure 8:
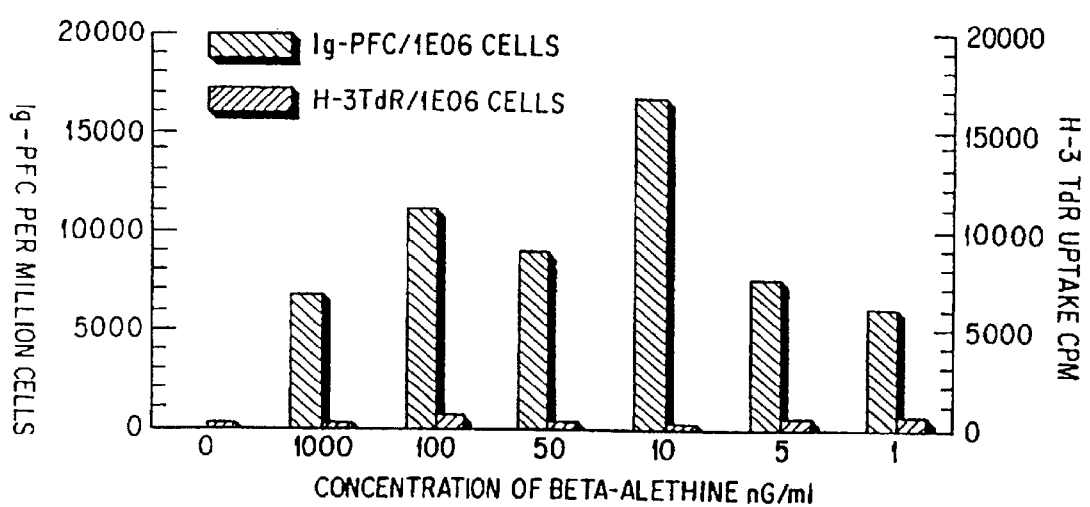

FIGS. 7, 8, and 9 illustrate stimulation of antibody production by human and mice cells exposed to β-alethine.

5. DETAILED DESCRIPTION OF THE INVENTION

As indicated above, β-alethine is a known compound [$(H_2NCH_2CH_2 (C=O) NHCH_2CH_2S)_2$ and Formula I following], commonly produced by oxidation of the corresponding monosulfide, β-aletheine [$H_2NCH_2CH_2(C=O) NHCH_2CH_2SH$ and Formula II following], which is unstable in air and aqueous solutions (The Merck Index, 9th edition (#221), Merck & Co., Rahway, N.J., USA):

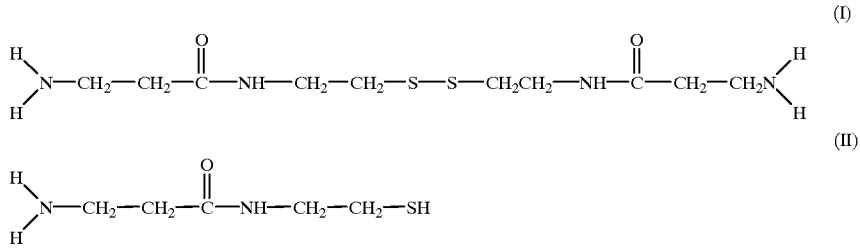

Both compounds are stabilized as their acid salts, particularly their hydrogen halide salts, and especially their hydrochloride salts. Various techniques for the synthesis of β-alethine based on deblocking of (N,N'-bis-carbobenzoxy)-blocked β-alethine are described in the literature (carbobenzoxy is often abbreviated as CBZ); however, most of the known procedures result in unsatisfactory yield or purity of product, or both. Accordingly, it is preferred that β-alethine for use in the processes of the invention be prepared by processes which ensure purity of product and preferably also maximize yield, for example by the process of the invention comprising coupling N-CBZ-blocked β-alanine to N-hydroxysuccinimide to produce the corresponding active ester, which is then coupled to cystamine prepared by oxidation of cysteamine with hydrogen peroxide; the product, CBZ-blocked β-alethine, is then recovered and deblocked. The process is described in detail in the Examples, and provides a high-yield, high-purity product suitable for pharmaceutical use.

According to the invention, β-alethine appears to regulate a set of generic differentiation mechanisms that are not cell-lineage specific and that are common to cells regardless of phenotypic specialization. Consistent with this premise, the use of β-alethine according to the invention as an anti-tumor agent is not significantly dosage-dependent with respect to cell lineage, phenotype, or point of intervention in the cell cycle, except as noted below. For in vivo applications, from about 10 pg of β-alethine/kg of body weight is recommended, particularly amounts from about 10 pg/kg up to about 200 μg/kg, and more particularly, up to about 100 μg/kg, which may be administered by any customary route including parenterally (such as i.p.) or anally in conjunction with conventional carriers such as physiological saline for non-oral routes, or orally with appropriate enterocoating. The compounds are preferably administered on a daily or alternate-day regimen as described more fully below, until the desired results are achieved, although other regimens, such as weekly or biweekly regimens may suffice, particularly when results are apparent; decreases in dosages as normalization progresses or tumor burden is reduced may be suitable, and may be preferable to avoid too-rapid regression of tumors accompanied by excessive physiological stress on the organism. Use of amounts of β-alethine substantially in excess of those required to obtain differentiation, normalization of cell function, decrease of tumor burden, or other results noted herein are not recommended, as excessive dosages may be counterproductive or at least ineffective. For in vitro applications for normalization of neoplastic cells, dosages starting from about 10 pg/ml culture are suggested, with daily or bi-daily replenishment.

It is contemplated that β-alethine is useful for the treatment of neoplasias of cells of living organisms in general, including mammalian, especially human, reptilian, avian, and plant cells, owing to the commonality of results obtained with corresponding dosages observed in experiments reported herein and unreported experiments. According to the invention, β-alethine comprises an anti-tumor compound which normalizes cell function (i.e., increases insufficient function or decreases excess function). β-alethine specifically functions to (1) inhibit tumor growth, especially that of malignant tumors; (2) regress tumors, especially malignant tumors; (3) inhibit tumor metastasis; and (4) normalize growth characteristics of neoplastic cells; and/or (5) improve recognition and/or elimination of neoplastic cells.

In cancer applications, neoplastic cells or immunocytes, or both neoplastic cells and immunocytes, are exposed to β-alethine to promote differentiation of the cells and normalize the cell cycle. Treatment of tumor cells is effectively segregated from treatment of the immunocytes by removing immunocytes from the afflicted mammal, including humans. The immunocytes are then treated in culture with β-alethine, or with a combination of β-alethine and tumor cells derived from the afflicted mammal, until either the immunocytes are activated, or the tumor cells are completely attenuated for health reasons, respectively. The activated immunocytes preferably devoid of metastatic tumor cells are then reinjected into the mammal. β-alethine is useful in vivo for reducing soft (hematolymphoid) tumor burden, particularly in mammals, especially in humans, and inhibiting intravascularization of tumor cells, especially cells of metastasizing tumors. The compounds are thus useful for reducing tumor burden, by inhibiting tumor growth or by inhibiting tumor metastasis, or both. In particular, β-alethine is contemplated to be useful in the treatment of numerous soft and lymphoid malignant tumors, such as lymphomas; leukemias; hepatocellular tumors; liver tumors; and Hodgkin's disease; especially tumors such as myelomas. β-alethine is contemplated inter alia as useful in the treatment of neoplasia 1) prophylactically; 2) as a primary therapy for inhibiting tumor growth, particularly that of slowly-growing tumors; and 3) as a supplemental therapy pursuant to surgical intervention for removal or debulking of tumors, particularly virulent or primary tumors. Treatment with β-alethine has been found to regress tumors, reduce tumor mass, inhibit tumor growth, inhibit tumor metastasis, and inhibit tumor ascites production.

It is recommended that anti-tumor therapy commence at the earliest tumor stage possible, particularly to avoid peripheral physiological complications caused by the presence or metastasis of large tumors. β-alethine for tumor therapy is administered by any convenient route as noted above, for example i.v. or i.p., in a suitable conventional carrier such as physiological saline at at least therapeutic threshold amounts; from about 1 ng/kg body weight up to about 100 μg/kg are particularly suitable, depending upon the stage of the tumor. Dosages toward the higher. end of the therapeutic range are recommended for Stage II tumors and above, whereas dosages toward the lower end of the range are suitable for Stage I or incipient tumors. For cancer prophylaxis, dosages ranging from about 10 pg/kg body weight, preferably from about 1 ng/kg up to about 100 μg/kg body weight are contemplated. Therapeutic regimens of alternate days for the dosages noted above for cancer treatment are suitable, and appear to be preferable, based on the observation that in vivo induction of biochemicals such as enzymes thought to be responsive to β-alethine therapy appear to follow chemical stimulation by about 48 hrs. Prophylactic regimens may be followed on a daily basis.

At least at the dosage levels indicated, β-alethine appears to be a substantially non-toxic compound in healthy mice, with no observed adverse side-effect.

For in vitro applications, immunocytes and optionally tumor cells removed by methods described in the prior art are treated by exposing the cells to an appropriate amount of β-alethine prior to reinjection of the immunocytes into the afflicted mammal according to methods described in the prior art. Techniques for removing and maintaining cells in culture (immunocytes in particular), treating these cells with immunopotentiating agents in cell culture, and reinjecting these immunopotentiated cells into mammals are described in the prior art, for example, *Immune Responses to Metastases* (volumes I and II, 1987, CRC Press, Boca Raton, Fla., USA), *Ann. Surg.* (201: 158–163, 1985), *New England J. Med.* (319: 1676–1680, 1988), *Cancer Immunol. Immunother.* (26: 1–10, 1988), Surgery (pp. 262–272, August 1986), and *Current Protocols in Immunology* (volumes 1 and 2, Green Publishing Associates and Wiley-Interscience, New York, N.Y., USA) incorporated herein by reference. Broadly suitable techniques for removing cells from the afflicted mammal include needle or core biopsies or surgical removal of organs, tumors, or humoral fluids. Outgrowth from needle biopsies, or treatment of core biopsies or tissues with collagenase or sieving through appropriately sized sterile meshes to disrupt organization of solid tissues, comprise exemplary methods for establishing cultures of cells, in vitro. According to the present invention, similarly removed cells are treated with β-alethine for an appropriate amount of time in cell culture, and similarly reinjected into the afflicted mammal, the improvement in technique being the treatment of the cells with β-alethine. In certain instances, it may be desirable to remove β-alethine prior to reinjection of the immunocytes into the afflicted mammal by washing the cells as described in the prior art. For in vitro applications according to the invention, exposure of the cells to from about 10 pg β-alethine included per ml of cell culture media (based on a density of from about $10^5$ to about $10^7$ cells/ml) for an appropriate amount of time, for example from about 30 minutes to four weeks or until the desired immunopotention is evident as described in the prior art, is suggested. In particular, in vitro stimulation of antibody production by human peripheral blood leukocytes or murine splenocytes is most efficacious between 10 pg and 1 μg β-alethine/ml cell culture after about four to six days of exposure (see, e.g, Examples V and VI). The culture should be replenished with the compound as necessary, generally on a daily basis; treatment on an alternate-day or biweekly basis may suffice, depending upon the desired results. During this period, exposure of the cells to immunogenic substances or cells other than extracted tumor cells, such as allogeneic serum proteins in the cell culture media, should be minimized to preclude diversion of the immunological response to non-tumor targets.

6. EXAMPLES

I. Preparation of β-alethine:

β-alethine was produced by deblocking N,N'-bis-carbobenzoxy (CBZ) blocked β-alethine produced as follows:

A. Preparation of N,N'-bis-(CBZ)-β-alethine or 5,5-Bis-[N-carbobenzoxy-β-alanyl]-2-aminoethyl] disulfide.

A solution of dicyclohexylcarbodiimide (23.3 g) was added to a solution of N-CBZ-β-alanine (24.84 g) and N-hydroxy-succinimide (12.92 g) in a total volume of about 500 ml of dry 10% acetonitrile in dichloromethane. Dicyclohexylurea (24.51 g) precipitated as a by-product upon formation of the active ester. The active ester was dried to an oil and triturated with anhydrous ethyl ether. The precipitate was resuspended in dichloromethane and additional dicyclohexylurea was allowed to precipitate. The resulting dichloromethane solution of active ester was filtered and added to a previously prepared solution of cystamine (8.5 g). The desired product, N,N'-bis-(CBZ)-β-alethine precipitated from this mixture. The mother liquor, anhydrous ether, dichloromethane extracts of the product, and the anhydrous ether extract of the active ester recovered above were dried and recombined to augment the yield of product. The product was substantially insoluble in water, hot (above about 70° C.) ethyl acetate, and hot (above about 30° C.) ether, and these can be used to further extract impurities. The product can also be recrystallized from dimethyl sulfoxide with acetonitrile or water, and again rinsed with ethyl acetate and ether. The latter process results in a 1° C. increase in product melting point, from 180 to 181° C. (uncorrected). Yields of N,N'-bis-(CBZ)-β-alethine of up to theoretical yields are contemplated; yields of 85–90% of theory have been routinely obtained. When dried over $P_2OS_5$, in vacuo, the product appears to retain one mole equivalent of water, and was analyzed accordingly as the monohydrate.

Anal. Calcd. for $C_{26}H_{34}N_4O_6S_2.H_2O$: C, 53.78; H, 6.25; N, 9.65.

Found: C, 54.23; H, 6.56; N, 9.66. Sample analyzed by Ruby Ju, Department of Chemistry, University of New Mexico, Albuquerque, N.M.

B. Deblocking of CBZ-blocked β-alethine obtained from I.A., above [preparation of β-alethine.2HCl; or N,N'-bis-(β-alanyl)-cystamine; or N,N'-bis-(β-alanyl-2-aminoethyl) disulfide].

Complete removal of the carbobenzoxy group was accomplished according to procedures described in *J.Am. .Chem.Soc.* 86: 1202–1206 (1964), incorporated herein by reference. After deblocking with four equivalents of hydrogen bromide in glacial acetic acid per mole of the N,N'-bis-(CBZ)-β-alethine for 14 hours, the β-alethine was purified by precipitation with acetonitrile, rinsing with anhydrous ethyl ether, resuspension in water and filtering, and precipitation of the mixed salt product with acetonitrile. Initial yields were in excess of 80% of theoretical maximum yields. β-alethine was converted to the hydrochloride salt by passing the preparation over a 30 ml×15 cm long column of Dowex AG 1×8 (chloride form) (Dow Chemical Corp., Midland, Mich., USA) which had been previously prepared by eluting with 1M KCl and rinsing thoroughly with DI (deionized) water. Neutralization with Ca(OH)$_2$ and recrystallization of the β-alethine HCl from water with acetonitrile resulted in fine needles which melted at 224–225° C. (uncorrected).

Anal. Calcd. for Calcd for $C_{10}H_{22}N_4O_2S_2.2HCl$: C, 32.69; H, 6.59; N, 15.25.

Found: C, 32.52; H, 6.69; N, 15.32. Sample analyzed by Ruby Ju, Dept. of Chemistry, University of New Mexico, Albuquerque, N.M.

C. Characterization of β-alethine: [$^{13}$C]-NMR; [$^1$H]-NMR; and IR spectra of β-alethine.

| | a<br>S—CH$_2$ | b<br>CH$_2$—N | c<br>H—N—C=O | d<br>O—C—CH$_2$ | e<br>CH$_2$—N | f |
|---|---|---|---|---|---|---|
| | | | | | ⟶ | —N—H / \ H + H |
| | | | [$^{13}$C]-NMR | | | |
| β-alethine | 37.59 | 39.04 | 172.79 | 32.9 | 36.71 | — |
| | | | [$^1$H]-NMR | | | |
| β-alethine | 2.524 | 3.094 | | 2.694 | 3.367 | — |
| bis-(CBZ)-β-alethine | | | ⟶ | | | H—N—C=O \ O—R |
| (DMSO) | 2.740 | 3.309 | 8.085 | 2.254 | 3.192 | 7.24 |
| | a | b | c | d | e | f |

-continued

| | | | IR (cm$^{-1}$) | | |
|---|---|---|---|---|---|
| a | b | c | d | e | f |
| | | | | ═> | —N—H  /  H + H |
| β-alethine | 660w | | 3250w | — | 3270v |
| | | | 1555w-s | | 2970s-w |
| | | | 1286m | | 1462s |
| | | | 1620s | | 1620s |
| | | | | | 1128s |
| | | | | ═> | H—N—C═O  \  O—R |
| bis-(CBZ)-β-alethine | | | | | |
| | — | | 3345s | — | 3345s |
| | | | 1545m | | 1535s |
| | | | 1640s | | 1270m |
| | | | | | 1682s |
| a | b | c | d | e | f |

(R is a benzyl moiety in this table.)

β-alethine is unusual in that changes in pH [neutralization with Ca(OH)$_2$] cause pronounced shifts in the positions and intensities of IR bands.

Peaks (HCl salt): 3270s, 3170s, 2970s, 2700w, 2550w, 2020w, 1657s, 1595m, 1560s, 1450s, 1409m, 1390w, 1354w, 1325m, 1300w, shoulder/1252m/shoulder, 1188m, 1129m, 1097m, 1079w, 1030w, 950w, 905w, 829m.

Peaks (neutralized): 3250w, 3180w, 2940m/broad, 2375s, 2230s, 2157s, 1936w, 1620s, 1555w, 1462s, 1432 shoulder, 1400m, 1342m, 1286m, 1217m, 1188m, 1128s, 1020m, 810w, 719m, 660w.

Bis-(CBZ)-β-alethine displays few of the resonances present in β-alethine.

Peaks: 3345s, 3310s, 1682s, 1640s, 1545m shoulder, 1535s, 1450w, 1427w, 1375w, 1332m, 1270m, 1231m, 1178w, 1120w, 1030m/broad.

II. Inoculation of Mice with NS-1 Myeloma Cells.

NS-1 myeloma cells (ATCC TIB 18, P3/NS1/1-Ag4-1) were employed as inoculant; these cells have proven to be about 90% effective in establishing myelomas in mice according to the exemplified procedure, and the untreated myelomas are substantially fatal within about two weeks.

The cells were grown for several passages (preferably one week) in a sterile environment consisting of RPMI 1640 (Whittaker M. A. Bioproducts, Walkersville, Md., USA) containing 10% fetal calf serum (Hyclone Laboratories, Logan, Utah, USA), 2 mM L-glutamine, 5,000 units of penicillin, and 5 mg streptomycin in 75 cm$^2$ polystyrene tissue-culture flasks (Corning Glassworks, Corning, N.Y., USA) in a humidified chamber at 37° C. and under 6% CO$_2$. To assure NS-1 propagation in vivo it is essential to remove DMSO (the cryostatic agent dimethyl sulfoxide) through several medium changes and dilutions; this also serves to maintain the cells in log-phase growth. Female BALBc/J mice were injected i.p. with 10$^4$ cells in 0.1 ml of standard phosphate-buffered saline as soon as possible after weaning, transport, and indexing, as it has been found that the NS-1 cell line employed does not generally perform optimally in animals which are mature or which have equilibrated with their environment. The mice were maintained with Wayne Rodent Blox (Wayne Research Animal Diets, Chicago, Ill., USA) ad lib. and tap water.

III. Treatment of Inoculated Mice (Example II) with β-alethine (early intervention).

A. Concentrations of β-alethine as obtained above (Example I) of 1 ng/kg, 1 pg/kg, 10 μg/kg, and 100 μg/kg (based on the body weight of the inoculated mice) were injected i.p. in 0.1 ml physiological saline starting the second day after tumor inoculation (day 2), and continuing every Monday, Wednesday, and Friday through day 47. This regimen was predicated on the observation that enzymes thought responsive to these compounds and which may play a role in the reported results are induced 48 hours after chemical stimulation. The inoculated mice were compared to a) untreated controls and b) to carrier-injected (saline-injected) controls.

Figure 1:
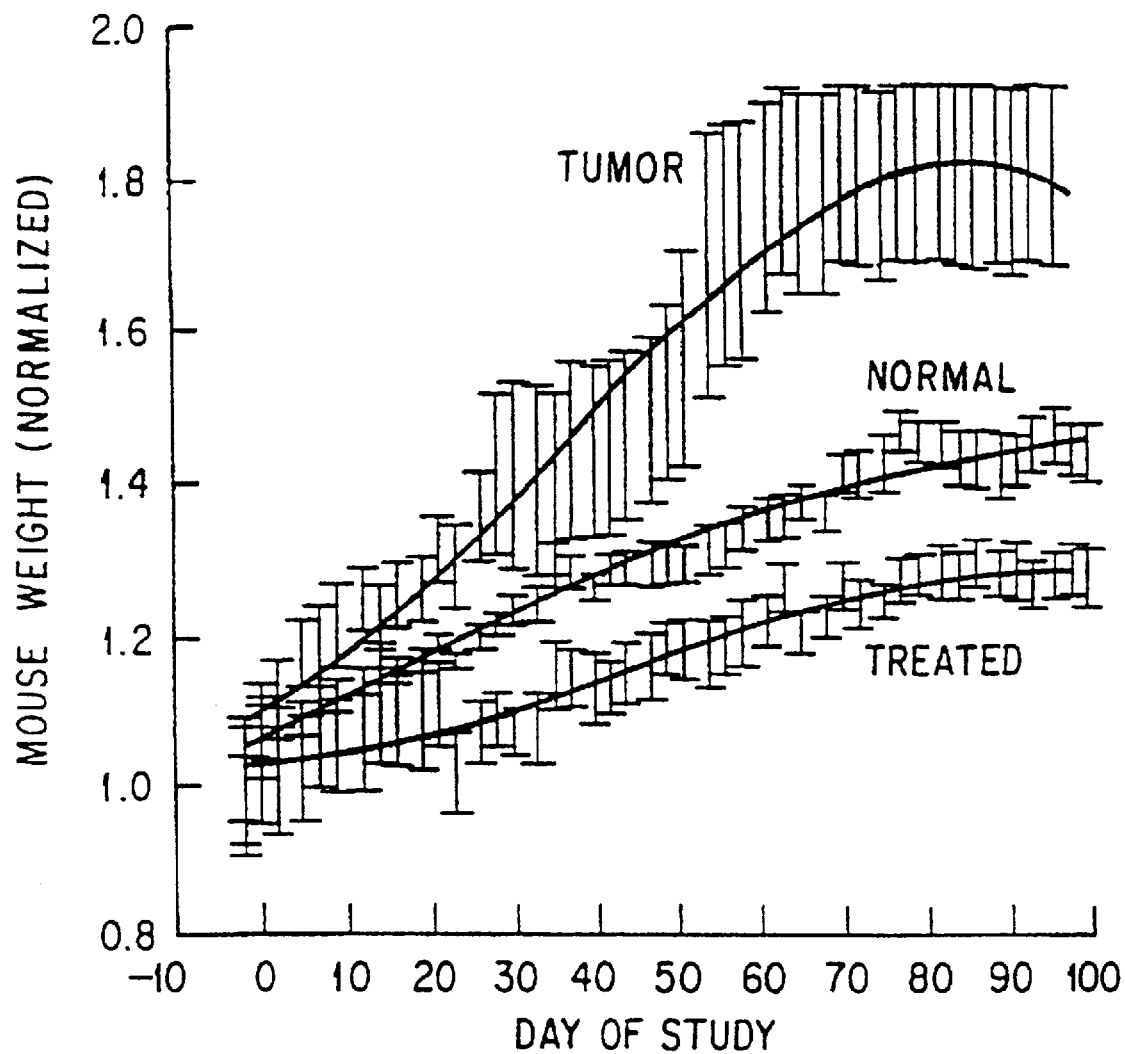
FIGS. 1–3 illustrate early and late tumor development in mice inoculated with non-secreting myeloma cells (NS-1) and treated with varying doses of β-alethine.
Figure 2:
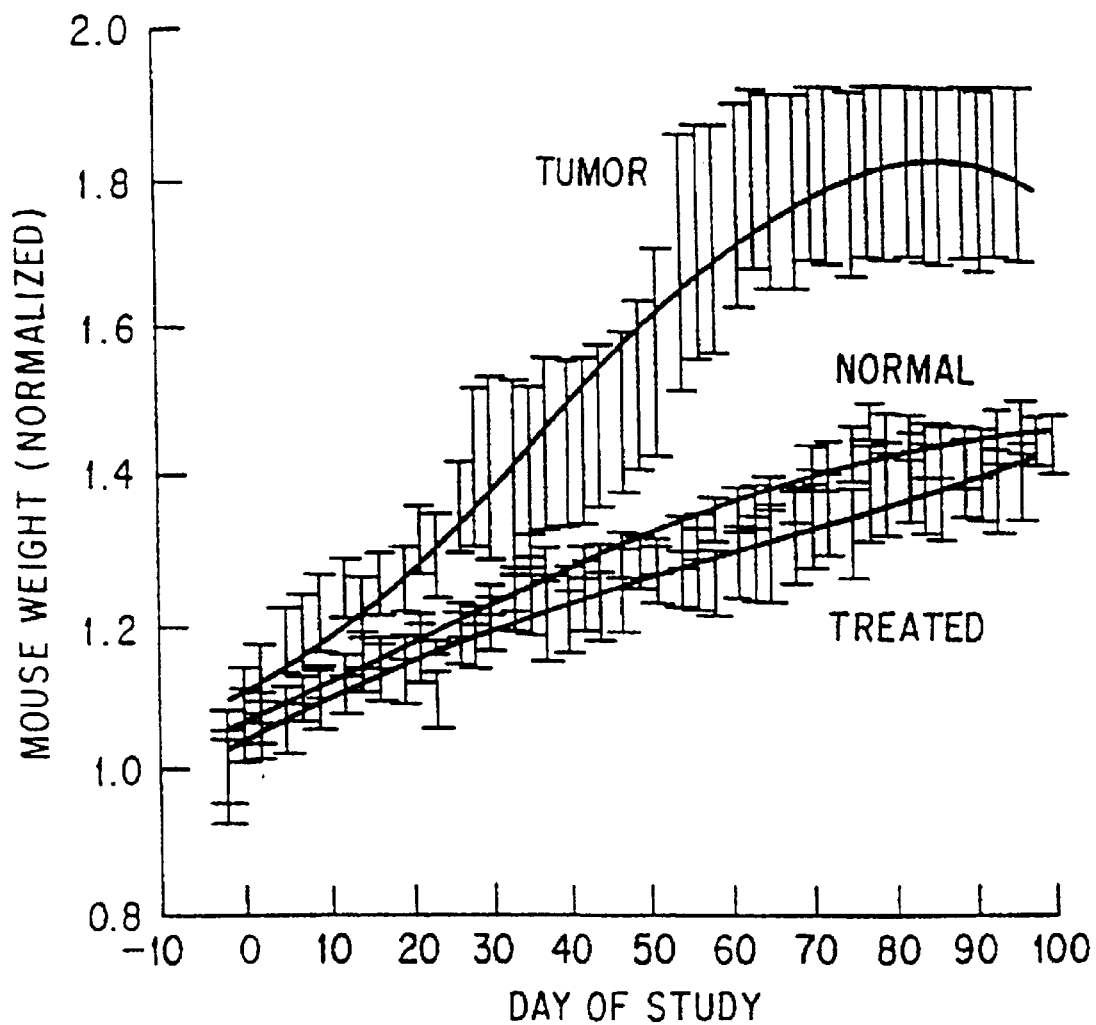
Figure 3:
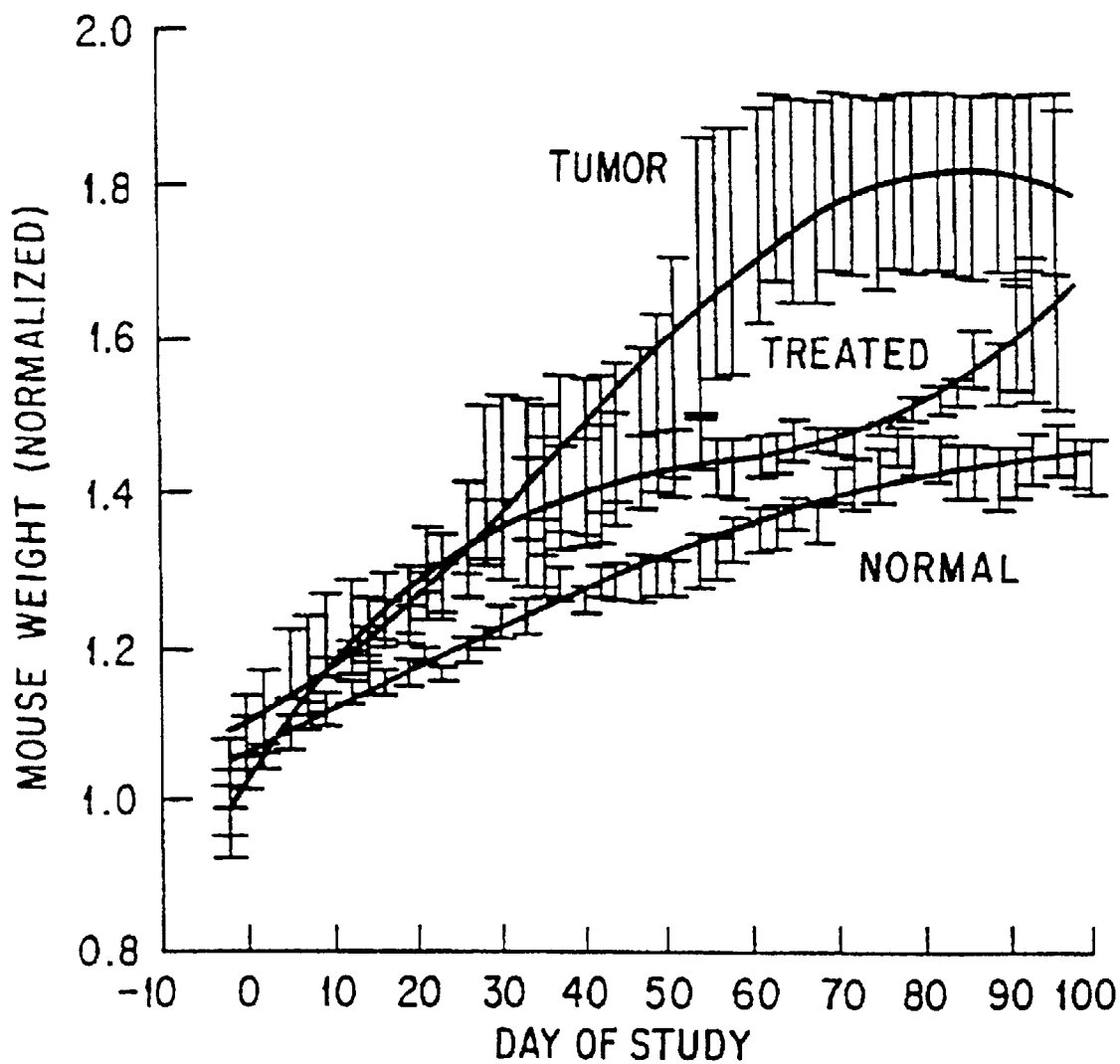
Figure 6:
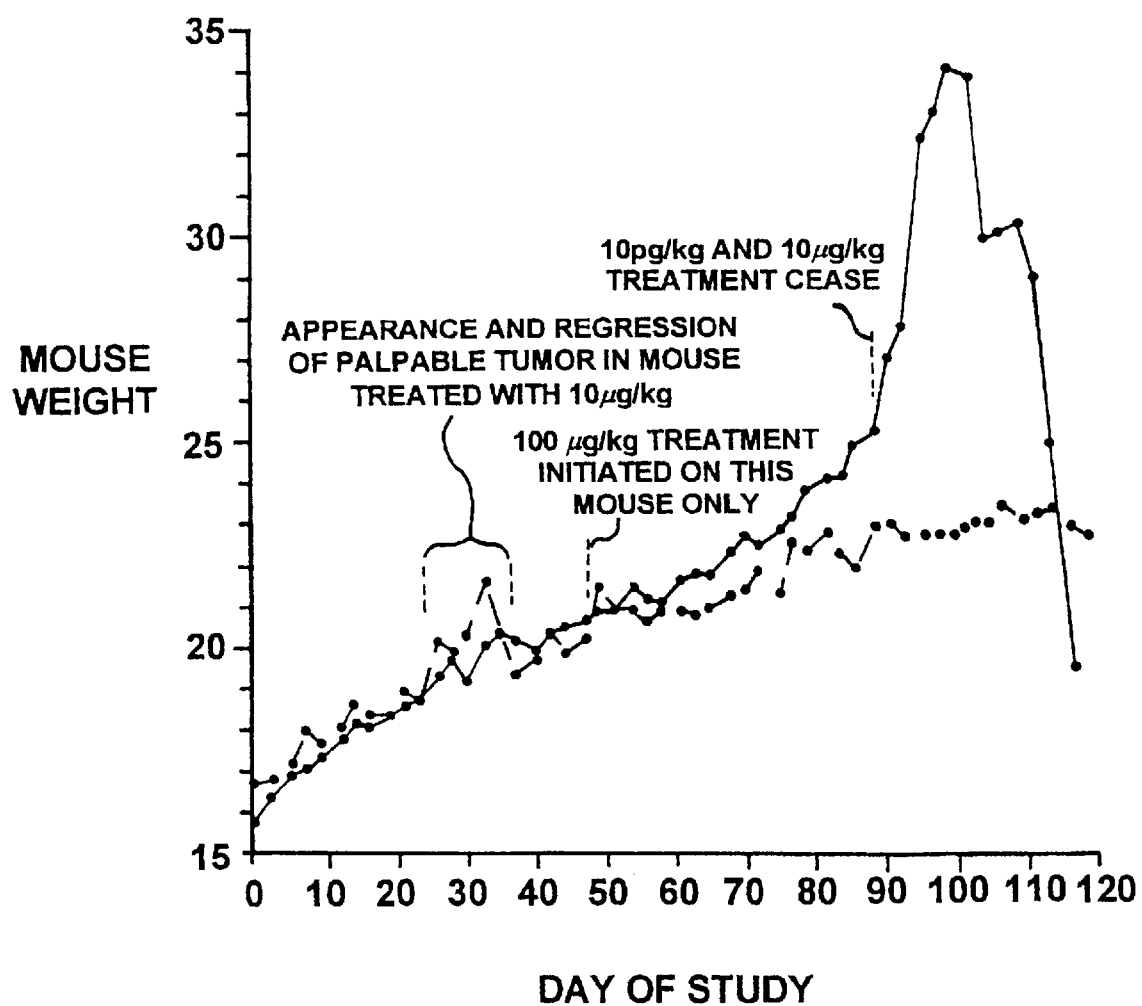
FIG. 6 illustrates modulation of tumor in two mice with differing amounts of β-alethine.

B. Conclusions

β-alethine is effective for preventing the onset of NS-1 myeloma in BALBc/J mice over the concentration range from 10 pg β-alethine/kg mouse to 100 μg/kg mouse. Without treatment, 75% of the mice in the experiment either had to be euthanized or died as the result of tumor development. At doses of β-alethine below the effective threshold [i.e., below about 10 pg/kg, or at about 10 pg/kg or 1 ng/kg (data not illustrated for the latter)] one-third to two-thirds of the animals ultimately contracted tumor. At dosages approaching the maximal effective dose (i.e., above about 10 μg/kg, or at about 10 μg/kg or 100 μg/kg), only one mouse developed a palpable tumor, which persisted for 20 days but eventually regressed. FIGS. 1–3 illustrate early and late tumor development (based on weight of mouse not attributable to normal weight gain) in mice treated with decreasing concentrations of β-alethine (10 μg, 10 μg, and 10 pg per kg mouse, respectively). In FIG. 3, the biphasic curve in the center illustrates early and late tumor development in these mice and corresponds to two deaths at this dosage (10 pg/kg mouse) of β-alethine which is the therapeutic minimal threshold for this compound in this model (FIG. 6). Normal weight gain of the mice is slightly inhibited at 100 μg/kg (FIG. 1), but not significantly at 10 μg/kg (FIG. 2). At 10 μg/kg (FIG. 2) one mouse developed a palpable tumor which persisted for 20 days but eventually regressed. At effective dosages of the antineoplastic compound β-alethine (from about 10 pg/kg body weight to about 10 μg/kg body weight), there is a striking difference between the weights of the mice (reflecting tumor burden) in the untreated control group (the vehicle-injected control group), compared with the mice in the treatment group.

Figure 4:
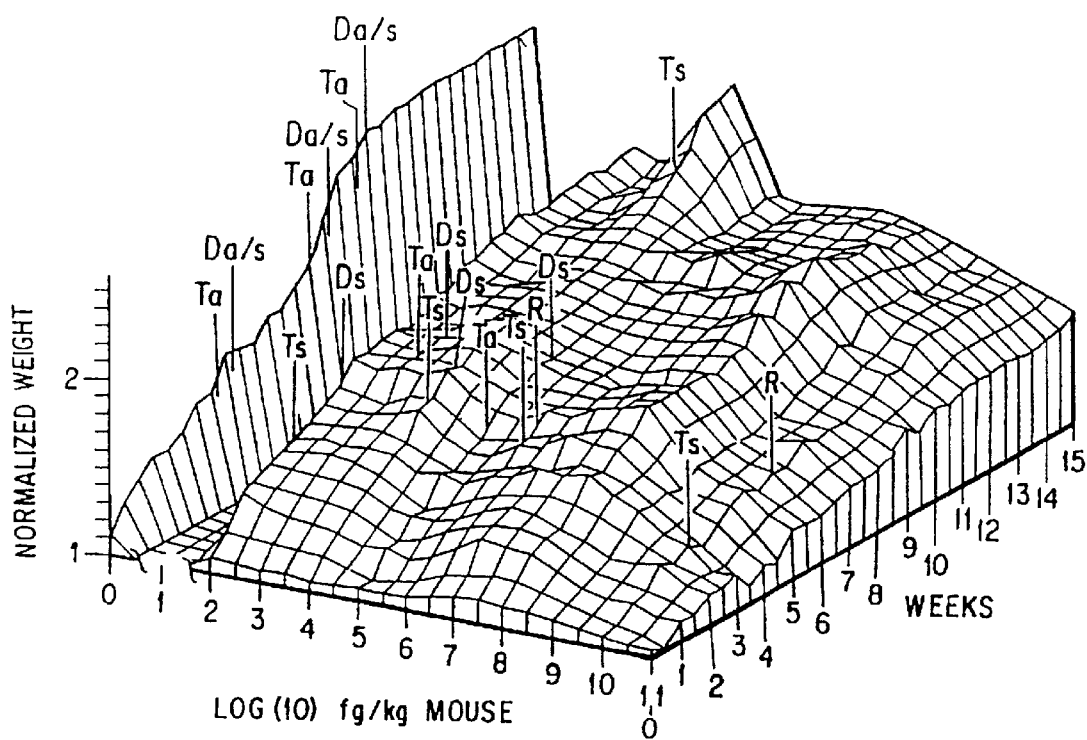
FIG. 4 is a three-dimensional composite of the data of FIGS. 1–3.
Figure 5:
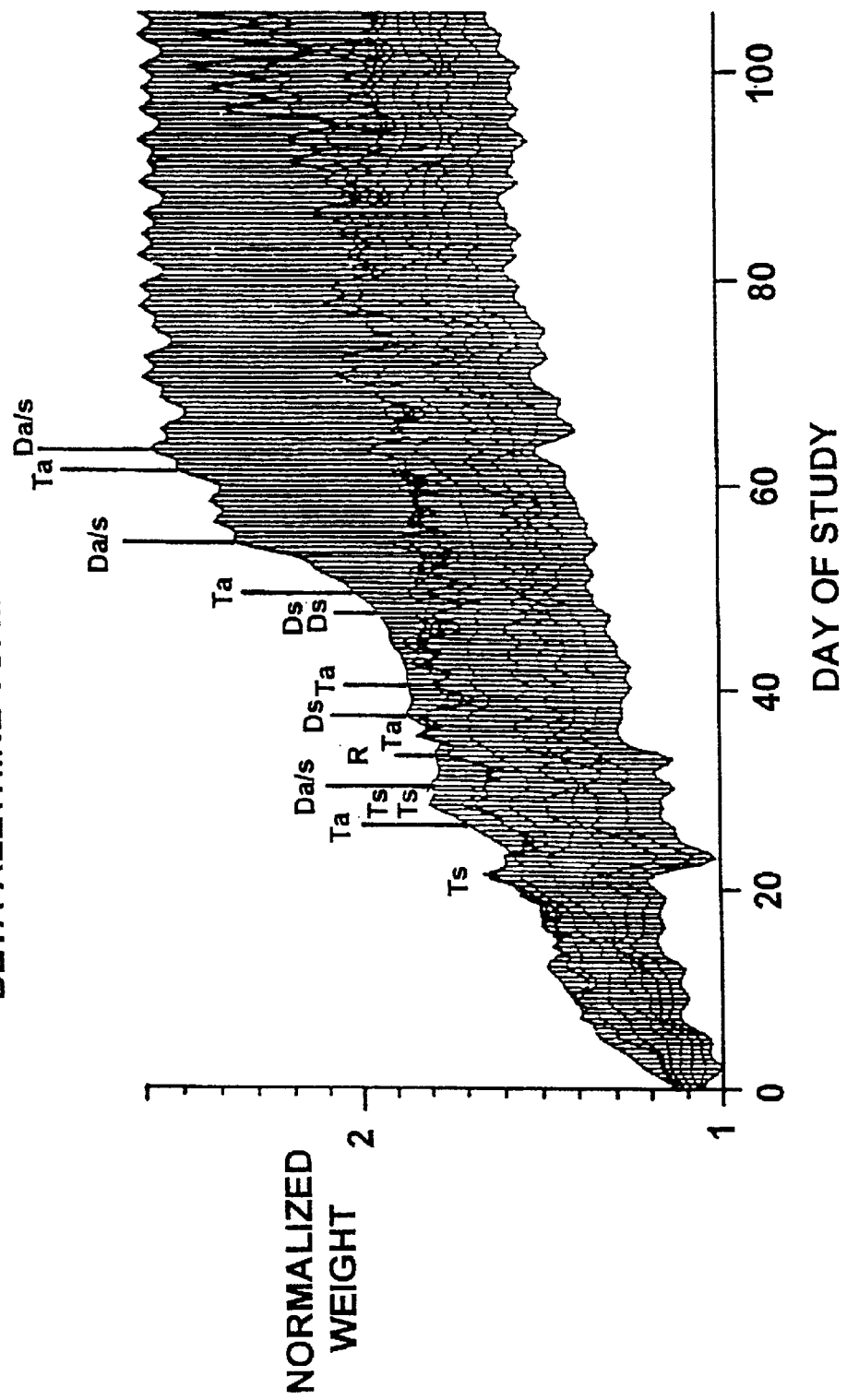
FIG. 5 is a 85 degree clockwise rotation of the illustration of FIG. 4.

The effectiveness of β-alethine in the treatment of NS-1 myeloma is further illustrated in FIG. 4, comprising a three-dimensional representation of the study; and in FIG. 5, comprising a 85° clockwise rotation of the illustration of FIG. 4, with higher doses of the drug in the front to no doses of the drug in the back. The controls inoculated with tumor (far left, FIG. 4) gain tumor and therefore weight (Z-axis) at an accelerated rate with respect to the day of the study (Y-axis). Mice receiving high doses of β-alethine (far right) develop at a near-normal rate and show no signs of chronic tumor. Ridges or increases in elevation illustrate tumor development at the lower concentrations (farther left on the X-axis) which are coded for the morphology of the developing tumor (Ta=ascites and Ts=solid tumors) and for deaths resulting from either ascites or solid tumors (Da or Ds respectively). Complete regression is indicated by R at the point at which the tumor is no longer palpable. When normalized to the initial weights of the mice in the control group and plotted (analyzed as in FIGS. 1–5), control mice (physiological saline injections only) displayed normal growth and development approximating the growth and development of the mice receiving tumor and 10 μg β-alethine/kg mouse (FIGS. 2 and 4). This is further illustrated in FIG. 6 in a mouse in which a tumor is modulated with different concentrations of β-alethine (below). The only departure from the normal growth curve coincides with the appearance and disappearance of a palpable tumor.

A tumor appeared and regressed without any signs of malaise in a mouse undergoing a therapy of 10 μg/kg β-alethine (FIG. 2). Tumors developing in untreated controls with some exceptions typically promoted ascites development, while tumors developing in mice undergoing therapy with β-alethine were with few exceptions solid masses; since it thus appears that β-alethine promotes consolidation of tumor into discrete masses, β-alethine is projected to be valuable in the design of treatment regimens involving surgical debulking.

IV. Treatment of Inoculated Mice (Example II) with β-alethine (late intervention).

A single mouse developing a tumor late in the experiment (at 4 on the X-axis, FIG. 4, approximately 40 days after the 10 pg β-alethine/kg mouse treatment was discontinued) was treated with 100 μg β-alethine/kg mouse to determine the effect of late therapeutic intervention on the treatment of the myeloma (FIG. 6). Massive log-phase growth of tumor persisted along the right side of the mouse from shoulder to hip and in the abdomen for 10 to 14 days after treatment with the higher dose was begun, indicating pronounced infiltration of the tumor into extra-peritoneal tissues, and a considerable lag phase before the treatment became effective. The growth then ceased, and was followed by rapid reduction of both the tumor mass and the weight of the mouse. There was a brief period in which the malaise subsided and the mouse's rough coat improved. This coincided with a temporary stabilization (approximately 1 week) of the mouse's weight suggesting that the tumor also stabilized during this time. This was followed by another precipitous drop in the mouse's weight and obvious decrease in the tumor masses. The mouse was euthanized when the weight returned to normal even though a palpable mass remained in the abdomen. At the time the mouse was euthanized, phlebitis was evident in the extremities, possibly resulting from the processing of the tumor equivalent of roughly 10% of the body weight per day. After correcting for necrosis evident histologically, it was estimated that between 85 and 90% of the original tumor was either necrotic or resorbed at the time of euthanasia. Considering the rate of resorption, there would have been complete regression of the tumor if the therapy had been maintained for the full month.

Wasting of the tumor and not the mouse proper was confirmed by weighing the debulked carcass. In this mouse, unlike untreated controls, there was no gross evidence of infiltration of organs by the tumor, and the remaining tumor appeared necrotic (yellowish-green and granular like an old sponge). Histological examination of the tissues indicated remaining tumor cells in the skeletal muscle adjacent to the abdominal wall, the subcutaneous tissue, and a mammary gland. Hepatic, urogenital, and gastrointestinal tumors, as well as a variety of other tumors, have been consistently observed in untreated mice, indicating the highly invasive and metastatic nature of the NS-1 cell line; however, in the treated mouse, none of the remaining organs contained tumor cells. An apparent pathological bone fracture was observed in this mouse, but no tumor cells were evident in the marrow of this bone. It was thus tentatively determined that the bone demineralized due to rapid growth of the tumor, a process requiring calcium and phosphate, and that subsequent rapid extraskeletal deposition of calcium phosphate as the tumor was resorbed resulted in the fracture.

Based on this and other studies, it is recommended that in the presence of aggressive neoplasia (e.g., stage II or above tumors), at least the primary tumor should be debulked surgically in conjunction with β-alethine therapy, preferably before or very soon after β-alethine therapy is commenced. It is further recommended that in some instances, β-alethine initial dosages of about 100 μg/kg used in late intervention therapy be gradually reduced to slow the resorptive process and permit the organism to adjust to the therapy. Gradual decreases of dosages (on an alternating 48 hour regimen) from about 100 μg/kg down to about 1 ng/kg are suggested as the tumor responds to the therapy.

V. Differentiation of a Peripheral Lymphoid Organ with β-alethine.

FIG. 7 illustrates data from a series of experiments designed to assess the effect of β-alethine on non-antigen-specific immunoglobulin synthesis and secretion in vitro by human peripheral blood leukocytes (HPBLs), generally characterized as a peripheral lymphoid organ primarily populated by medium-sized, mature lymphocytes. In these experiments, blood was taken from healthy male humans; the blood was then defibrinated on glass beads, and the leukocytes separated by centrifugation (buffy coat technique). Residual red blood cells were lysed with a brief treatment with 0.85% ammonium chloride. The leukocytes were counted and dispensed into 24 well tissue culture trays (LUX, Flow General, McClean, Md., USA) in 1 ml of RPMI 1640 basal medium supplemented with penicillin, streptomycin, 10% fetal calf serum, and L-glutamine. β-Alethine was added to test cultures at various concentrations in 30 microliter doses. The cells were harvested as indicated in FIG. 7 at various times between 72 and 144 hours of culture and tested for antibody production using a conventional protein-A facilitated plaque assay (A-PFC or Ig-PFC). In this assay, protein-A was covalently conjugated to washed sheep red blood cells (SRBC's) using chromium chloride in saline (6 mg/100 ml) and used as target in the plaque assay. In addition, aliquots of cells were also tested for proliferation status by treating them with 0.5 μCi of tritiated thymidine (6–9 Ci/mole) followed by assessing the level of incorporation of radioactivity into newly synthesized DNA. FIG. 7 shows that β-alethine stimulated the HPBLs to produce immunoglobulin in a dose-dependent manner at approximately 60 times the untreated control levels. The optimal concentration was about 5 nanograms/ml culture. The proliferation index indicated a low level of increased thymidine incorporation at 5 ng/ml doses. This 2-to 3-fold increase over background has minor significance as compared to truly proliferative stimulants such as LPS (lipopolysaccharide) or PHA (phytohemagglutinin), which under similar conditions result in the incorporation of about 200,000 cpm of radioactivity, approximately 100 to 200-fold that of control levels. It was concluded that the level of proliferation observed in the experiment was attributable to differentiation-dependent proliferation rather than to independent proliferative processes stimulated by β-alethine, or to an increase in both the survival of cells and the retentive capacity for deoxyribonucleic acids associated with viable cells.

VI. Differentiation of a Central Lymphoid Organ with β-alethine.

FIG. 8 shows data from a series of experiments designed to study the effect of β-alethine on murine splenocyte production of non-specific immunoglobulin. The assays and culture techniques were the same as those described above (Example V) for the HPBL model. The animals, 4 to 6 week old female BALBc/J mice, were sacrificed by cervical dislocation, and their spleens aseptically removed and pressed through 90 mesh stainless steel screens. After several washes with the complete medium the cells were counted and dispensed into the 24 well trays and test cultures were dosed with the β-alethine. These cultures were also harvested over various culture times of from 72 to 144 hours of culture, and tested for antibody production and proliferation, as shown in FIG. 8. FIG. 8 illustrates that β-alethine markedly stimulated the murine splenocytes to produce immunoglobulin in a dose-dependent manner, with an illustrated optimum at approximately 10 ng/ml dosages. In this case there was no significant stimulation of proliferation, based on the thymidine assay described in Example V.

VII. Differentiation of a Central Lymphoid Organ with β-alethine.

FIG. 9 shows data from a series of experiments designed to study the effect of β-alethine on murine splenocyte production of specific types of immunoglobulin. The assays and culture techniques were the same as those described in Examples V and VI for the murine splenocyte model, with the exception that rabbit antibodies which are specific for the gamma chain of mouse antibodies is used to detect murine splenocytes producing IgG. The plaque assay is described in detail in the prior art by N. K. Jerne, et. al., in *Transplant. Rev.* 18: 130–191 (1974) incorporated herein by reference. The animals, 4 to 6 week old female BALBc/J mice, were sacrificed by cervical dislocation, and their spleens aseptically removed and pressed through 90 mesh stainless steel screens. After several washes with the complete medium the cells were counted and dispensed into the 24 well trays (LUX, Flow General, McClean, Md., USA) in 1 ml of RPMI 1640 basal medium supplemented with penicillin, streptomycin, 10% fetal calf serum, and L-glutamine. β-alethine was added to test cultures at various concentrations in 30 microliter doses. The cells were harvested as indicated in FIG. 9 at various times between 72 and 144 hours of culture and tested for antibody production using a conventional protein-A facilitated plaque assay (A-PFC or Ig-PFC). In this assay, protein-A was covalently conjugated to washed sheep red blood cells (SRBC's) using chromium chloride in saline (6 mg/100 ml), and the conjugate was used as target in the plaque assay. FIG. 9 illustrates that β-alethine markedly stimulates the murine splenocytes to produce IgG in a dose-dependent manner, with an illustrated optimum at approximately 10 ng/ml dosages and about four days into the study.

What is claimed is:

1. A method of treating a non-hematolymphoid neoplasia sensitive to β-alethine in a mammal in need of such treatment comprising administering to said mammal an amount of β-alethine, or physiologically compatible salt thereof, sufficient of effect said treatment.

2. The method according to claim 1 wherein said neoplasia is a metastatic tumor.

3. The method according to claim 1 wherein said administered β-alethine inhibits tumor growth.

4. The method according to claim 1 wherein said β-alethine inhibits tumor metastasis.

5. The method according to claim 1 wherein β-alethine is administered intravenously.

6. The method according to claim 1 wherein β-alethine is administered intraperitoneally.

7. The method according to claim 1 wherein said amount is from about 1 ng/kg body weight to about 100 μg/kg body weight.

8. The method according to claim 1 wherein said neoplasia is a liver tumor, a mammary tumor, a urogenital tumor, a gastrointestinal tumor or a muscle tumor.

9. The method according to claim 8 wherein said neoplasia is a liver tumor.

10. The method according to claim 8 wherein said neoplasia is a mammary tumor.

11. The method according to claim 8 wherein said neoplasia is a urogenital tumor.

12. The method according to claim 8 wherein said neoplasia is a gastrointestinal tumor.

13. The method according to claim 8 wherein said neoplasia is a muscle tumor.

14. A method of treating a non-hematolymphoid neoplasia sensitive to β-alethine in a mammal in need of such treatment comprising:

i) removing immunocytes from said mammal and placing said immunocytes in a culture medium, ii) exposing said immunocytes to β-alethine, or a physiologically compatible salt thereof, and iii) reintroducing immunocytes resulting from step (ii) into said mammal, wherein, in step (ii), said immunocytes are exposed to β-alethine for a period of time and in an amount such that, upon said reintroduction, said immunocytes recognize and eliminate cells of said neoplasia, and wherein, in step (iii), said immunocytes are reintroduced in an amount sufficient to effect said treatment.

15. The method of claim 14, wherein the mammal is human.

16. The method of claim 14, wherein the immunocytes are additionally exposed to tumor cells extracted from the afflicted mammal prior to reinjection.

17. The method according to claim 14 wherein said amount of β-alethine is at least 10 pg per ml of said culture medium.

18. The method according to claim 14 wherein said amount of β-alethine is in the range of 10 pg/ml culture medium to 1 μg/ml culture medium.

19. The method according to claim 14 wherein said immunocytes are exposed to β-alethine for from 30 minutes to four weeks.

* * * * *